(12) United States Patent
Scrivens et al.

(10) Patent No.: US 6,819,408 B1
(45) Date of Patent: Nov. 16, 2004

(54) METHOD FOR OBTAINING A MONOLAYER OF DESIRED PARTICLES IN A LIQUID SAMPLE

(75) Inventors: Brian G. Scrivens, Colora, MD (US); Dwight Livingston, Fallston, MD (US); Robert S. Frank, Ellicott City, MD (US); Klaus W. Berndt, Timonium, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 278 days.

(21) Appl. No.: 09/671,524

(22) Filed: Sep. 27, 2000

(51) Int. Cl.[7] .......................... G01N 33/48; G01N 1/10
(52) U.S. Cl. ....................... 356/39; 356/246; 422/82.05; 422/101
(58) Field of Search ..................... 356/246, 39; 422/44, 422/58, 82.05, 99, 101, 102, 104, 255; 436/165; 435/287.1, 288.7; 250/428, 435, 438, 573, 576, 239

(56) References Cited

U.S. PATENT DOCUMENTS

| | | | | |
|---|---|---|---|---|
| 4,245,907 A | * | 1/1981 | Rosen | 356/244 |
| 4,790,640 A | * | 12/1988 | Nason | 359/396 |
| 5,164,598 A | * | 11/1992 | Hillman et al. | 250/341.3 |
| 5,466,384 A | * | 11/1995 | Prevost et al. | 210/787 |
| 5,635,358 A | * | 6/1997 | Wilding et al. | 435/7.2 |
| 5,700,695 A | * | 12/1997 | Yassinzadeh et al. | 436/180 |
| 6,106,483 A | * | 8/2000 | Guirguis | 600/562 |
| 6,387,325 B1 | * | 5/2002 | Keusch et al. | 422/50 |
| 6,448,088 B1 | * | 9/2002 | Levine et al. | 436/164 |
| 6,477,479 B1 | * | 11/2002 | Mansky et al. | 702/136 |

* cited by examiner

*Primary Examiner*—Zandra V. Smith
*Assistant Examiner*—Gordon J. Stock, Jr.
(74) *Attorney, Agent, or Firm*—Bruce S. Weintraub, Esq.

(57) ABSTRACT

The present invention relates to a method and apparatus for analyzing a blood or other biological fluid sample in a quiescent state without the need for additional diluting reagents or fluid streams passing through the apparatus during the analytic process, whereby particulate constituents of biological samples can be enumerated and inspected using an optical scanning instrument. Specifically, this invention relates to a method and apparatus for obtaining decreased cellular or particulate concentrations within the use of this system.

23 Claims, 4 Drawing Sheets

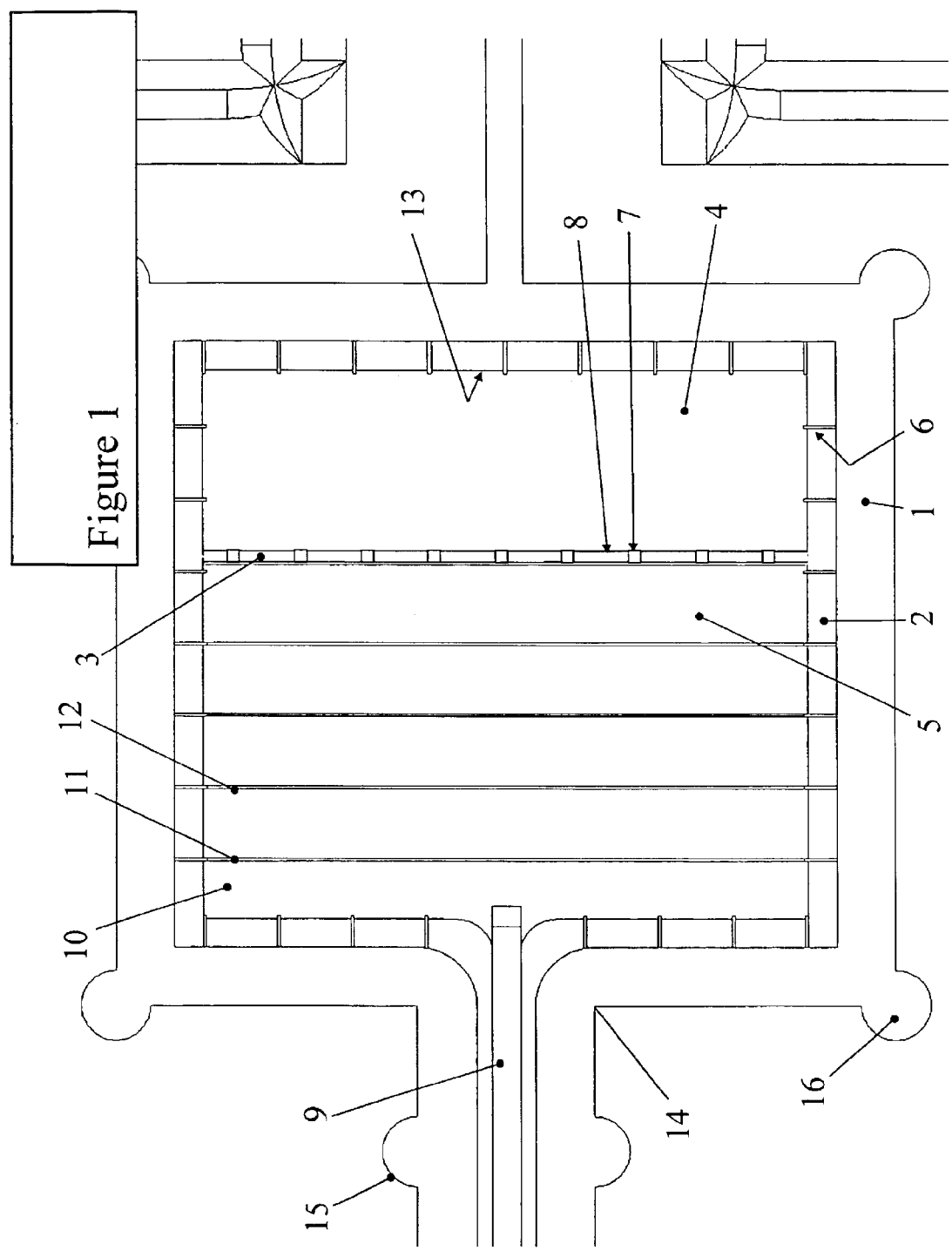

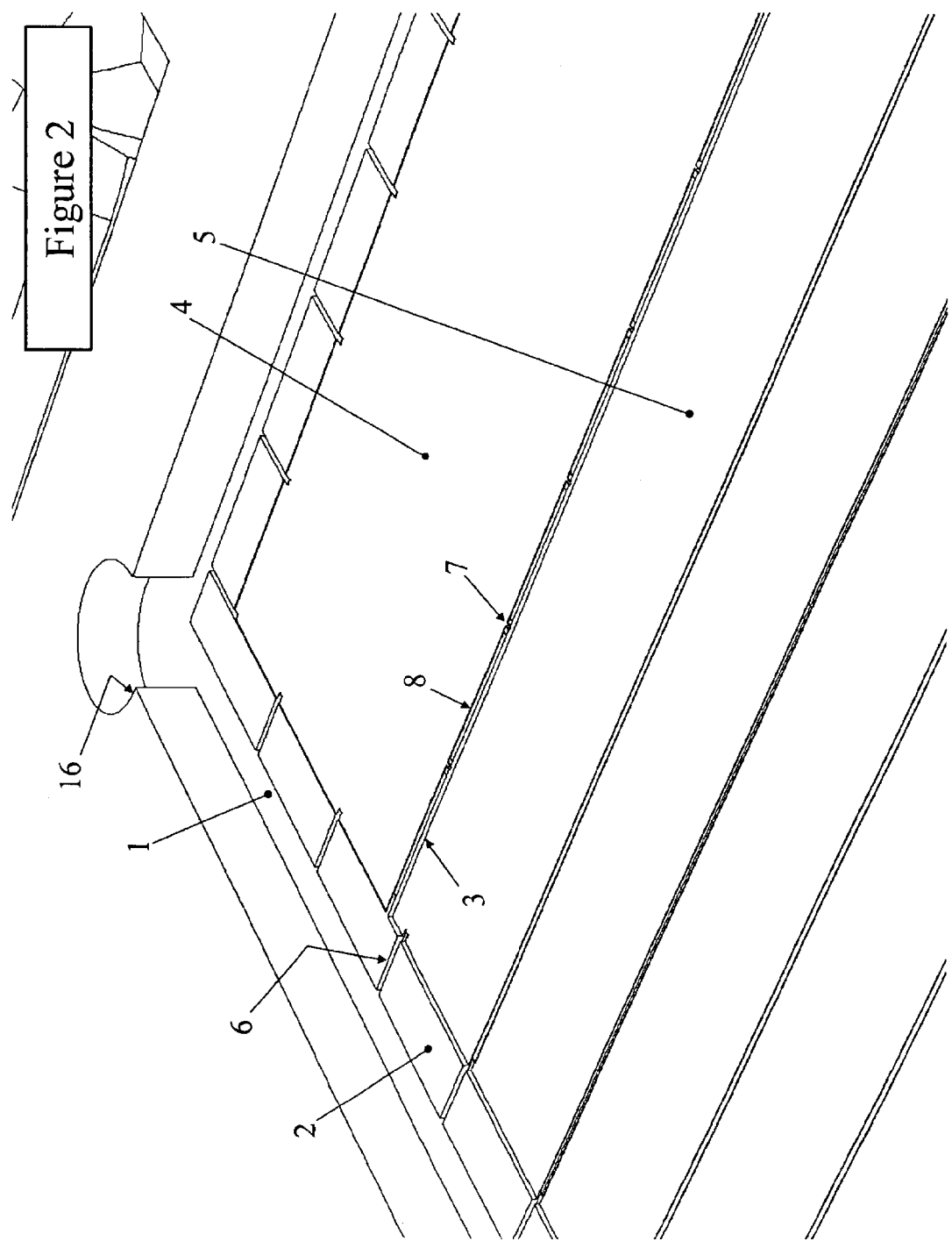

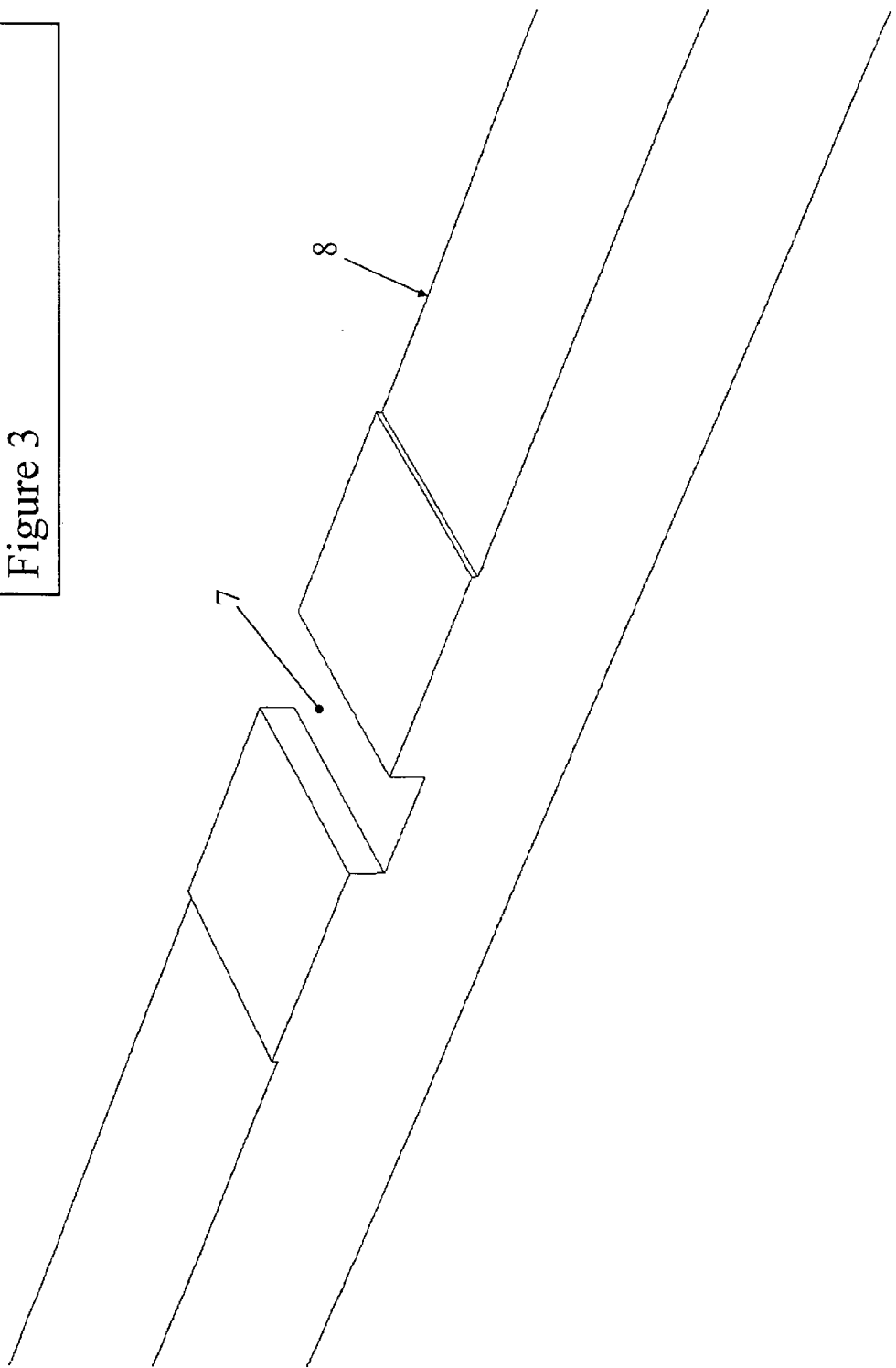

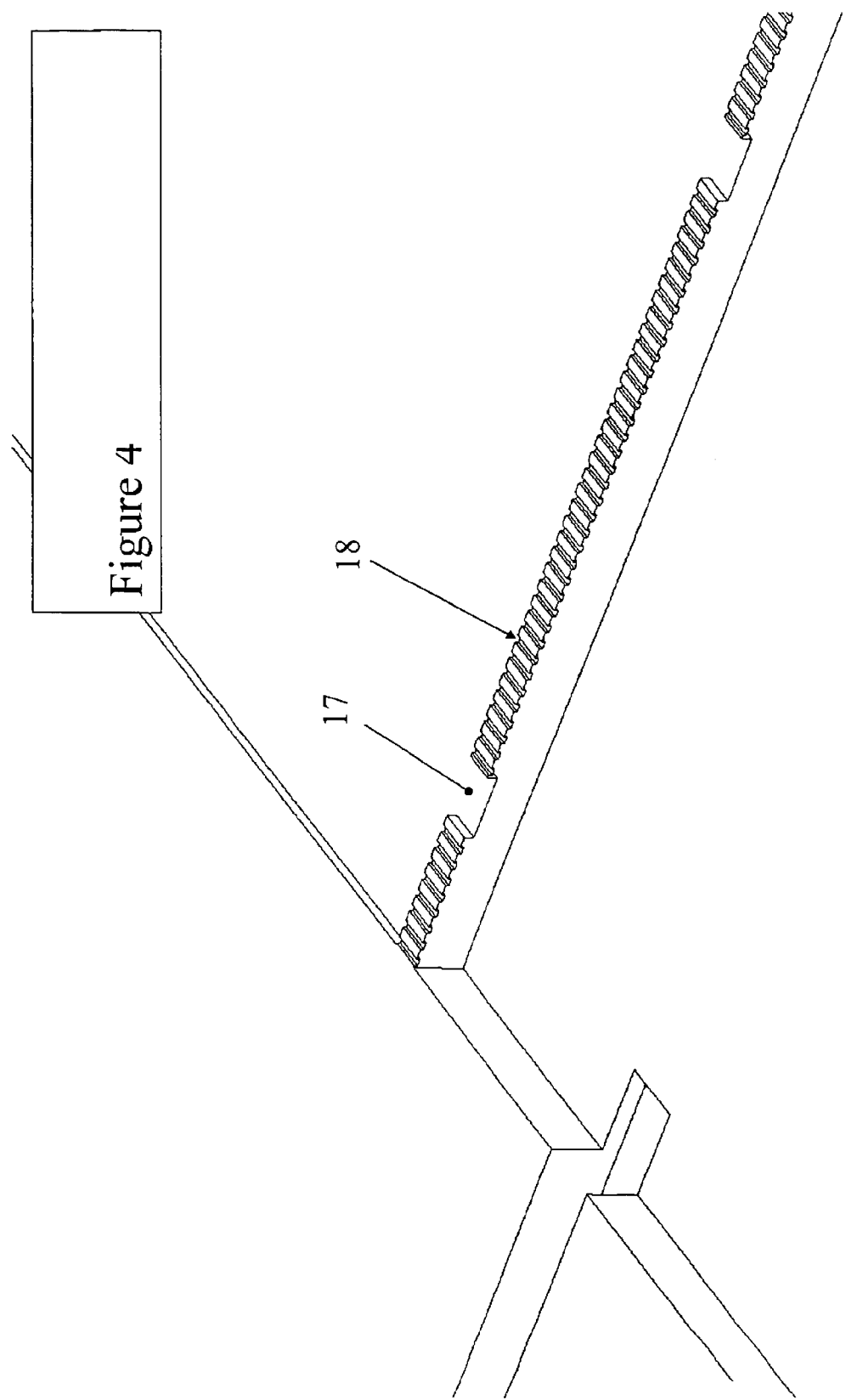

METHOD FOR OBTAINING A MONOLAYER OF DESIRED PARTICLES IN A LIQUID SAMPLE

FIELD OF THE INVENTION

The present invention relates to a method and apparatus for analyzing a blood or other biological fluid sample in a quiescent state without the need for additional diluting reagents or fluid streams passing through the apparatus during the analytic process, whereby particulate constituents of biological samples can be enumerated and inspected using an optical scanning instrument. Specifically, this invention relates to a method and apparatus for obtaining decreased cellular or particulate concentrations within the use of this system.

BACKGROUND OF THE INVENTION

The formation of appropriate cellular or particulate layers for later optical examination is important to many fields. One of these fields is hematology where several methods and devices have been described for obtaining clinically useful cell concentrations. The manual wedge smear yields results of acceptable accuracy when performed by a skilled clinician but is time consuming, expensive, and presents a biohazard risk. Instrumentation to perform a complete blood count, or "CBC", may also be used but has significant disadvantages which are, for example, in the complexity of operation, potential leak failures, low system reliability, and higher maintenance costs.

Cellular analysis by capillary volumetric scanning, for example, in U.S. Pat. Nos. 5,547,849 and 5,585,246, describes another method for obtaining several CBC parameters whereby controlled cell layers are obtained for optical scanning. However, it cannot measure cell morphology and red blood cell parameters. U.S. Pat. No. 4,790,640 discloses a device for separating certain selected cells by capturing them in a wedge shaped geometry, but the disadvantage of this device is that the resulting separation of cells are packed together making optical examination of individual cells difficult.

In pending U.S. Ser. Nos. 09/248,135 and 09/249,721, a method and apparatus for analyzing a blood or other biologic fluid sample in a quiescent state without the need for separate fluid streams passing through the blood sample during the analysis is described. Although this method simplifies the analysis procedure and yields the full complement of CBC parameters, it also possesses several disadvantages. One disadvantage of this apparatus is that the concentration of cells in the examination layer is not controlled except through chamber height which can lead to difficulties in optically examining cell volume and morphology. Another disadvantage of the aforementioned apparatus is that the field of cells may be too sparse in clinically relevant samples for scanning to be completed in a timely manner.

U.S. Pat. No. 4,022,521 describes a transparent specimen slide having precision projections on one side for accurate control of the specimen thickness allowing viewing of a monolayer of blood cells. A disadvantage of this apparatus is that it does not provide for control of the density of cells in the viewing area making optical identification of cellular species difficult. Another disadvantage of this apparatus is that the device is free to float, thereby allowing inaccuracies in defining the gap thickness and making volumetric measurement difficult.

It would therefore be desirable to have a better controlled and more reliable method and apparatus for obtaining the desired cellular concentrations in a blood or, other biologic sample without the need for a separate dilution step and addition of diluting fluids, as set forth in the present invention.

SUMMARY OF THE INVENTION

It is an objective of the present invention to provide separation-channels within a sample chamber having sufficient size and dimensions to allow a desired particle species to pass while excluding others, thereby arriving at a predetermined relative volume fraction of the desired particle.

It is another objective of the present invention to incorporate two or more channel sizes selected to allow one or more cell types of interest and the substantially liquid component of the sample to pass through them arriving at desired cell concentrations.

It is a further objective of the present invention to define the distance between adjoining parallel channels, or their dimensional pitch, and channel dimensions to effect the desired volume fraction of cells or particles of interest in the specimen.

It is also an objective of the present invention to regulate the volume fraction of cellular or particle components of a specimen by means of an array of channels which effect their selection by means of size exclusion during flow between two adjoining compartments.

It is an additional objective of the present invention to create regions of individual red blood cells (RBCs) or other particles and regions of red blood cell Rouleaux suitable for volumetric measurement of individual RBCs and hematocrit, respectively.

It is a further objective of the present invention to re-combine the fluid and particles, without introducing air bubbles into the specimen within the subsequent chamber.

It is yet a further objective of the present invention to guarantee an accurate spacing between two opposing containment walls to allow for the optimal formation of desired cellular regions and an accurate determination of the chamber thickness without relying on extraneous equipment and manipulations for height calibration.

It is another objective of the present invention to control the advance of a fluid meniscus during filling of the chamber by means of notches located in one containment wall of the chamber oriented substantially perpendicular to the advancing meniscus.

It is yet another objective of the present invention to stop the flow of fluid and contain its volume in the chamber while allowing for free passage and venting of air by means of a wall surrounding the chamber which contains a multiplicity of venting-channels interspersed along it and a moat surrounding the wall and fill channels.

BRIEF DESCRIPTION OF THE DRAWINGS

FIG. 1 is a plan view of the particle separation chamber with the upper containment wall removed showing four notches, and the one separation wall comprising two kinds of separation-channels and the adjacent cell examination area.

FIG. 2 is an isometric view of the bottom portion of the separation chamber showing the disposition of the separation channels in the separation wall.

FIG. 3 shows a detailed view of the separation channels.

FIG. 4 shows an isometric view of another embodiment of the separation channels.

DETAILED DESCRIPTION OF THE INVENTION

The present invention relates to a method and apparatus for obtaining a decreased cellular or particulate concentration within a sample chamber, without using added reagents or flow to substantially dilute the sample. Generally the only reagents used in performing the method of this invention are dyes, stains, and anticoagulants, which are not intended to dilute the specimen. Filling of the chamber results in a substantially quiescent sample ready for further examination. The apparatus includes a sample chamber which has opposing sample containment walls, at least one of which is transparent. The interior of the sample chamber is separated into two adjoining compartments by a separation wall. The two compartments are in fluid communication by means of an array of channels in the separation wall, that are aligned preferably parallel to each other. For the case of a chamber used to manipulate blood components one type of channel in the array is of sufficient size and dimensions to allow red blood cells (RBCs) to pass while excluding larger white blood cells (WBCs). The dimensions of the channel to create the desired size exclusion are nominally, in a preferred embodiment, 3 to 10 $\mu$m deep×5 to 50 $\mu$m wide. Such dimensions have been selected to effect the desired volume flow rate of red blood cell or particle containing sample.

Another type of channel in the array is of sufficient size and dimensions to exclude red blood cells and white blood cells from passing while allowing the liquid component of the specimen to pass freely. The dimensions of the channel to create the desired size exclusion are nominally, in a preferred embodiment, 0.5 to 1.5 $\mu$m deep×50 to 1000 $\mu$m wide. Dimensions within this range are selected to effect the desired volume flow rate of the liquid-only portion of the sample.

As the blood sample or particle containing specimen flows from the first compartment in the chamber and through the array of channels into the adjoining second compartment in the chamber the relative volume fraction of cells or particles is reduced. The two streams, one containing substantially undiluted blood or particles, and the other, a liquid-only fraction, recombine in the subsequent compartment in the chamber to form a liquid sample having a reduced volume fraction of cells or particles. The distance between two of the opposing sample containment walls in the subsequent second compartment in the chamber is sized so that individual red blood cells or other particles present in the sample will form a monolayer of the desired particles when the chamber is filled with the sample. In a preferred embodiment, the thickness of the second compartment in the chamber can be, generally, from about 1 to 7 $\mu$m. Since the sample containment walls are held at a fixed and accurately determined distance apart by the separation wall comprising the channel array, a monolayer of cells or particles is formed, regardless of the exact value of the compartment thickness. A further benefit of the invention is to provide a thickness within the compartments in the chamber during manufacture, which is more accurate than would otherwise be obtained. A compartment thickness within a certain range is required for obtaining cell monolayers necessary for volumetric measurement. Volumetric measurement of the cells requires the compartment thickness to be accurately known to be within +/-5% or preferably +/-3% or better to accomplish clinically relevant volumetric measurements.

The volume fraction of red blood cells is reduced by passing the whole blood sample through the separation channels allowing them to form a monolayer of individual cells regardless of normal manufacturing variations in compartment thickness. Since the volume fraction of the red blood cells is reduced, a large number of individual red blood cells will be presented for optical scanning. The thickness of the second compartment can be optimized for volumetric measurements of the cell components without the limitation of constraining the accuracy of compartment thickness simply to obtain cell monolayers. The separating wall acts to hold the opposing sample containment walls apart at a fixed and accurate distance.

The internal volume of the second thin-layer examination compartment in the chamber is small compared to the adjoining first compartment in the chamber, allowing the sample to become quiescent before the corresponding concentration effect in the first compartment can become large. This concentration effect has a negligible effect on the hematocrit, which can be accurately measured some distance away from the immediate vicinity of the separation wall. The thickness of the first compartment in the chamber is sized to create regions of red blood cell Rouleaux and cell-free plasma regions, which are useful for determination of sample hematocrit. In a preferred embodiment, the thickness of the first compartment can be in the range of between 10 and 50 $\mu$m.

As shown in FIGS. 1 and 2, the sample chamber is surrounded by a moat (1) and a wall (2) which has a multiplicity of venting-channels (6) displaced entirely around the chamber for adequate venting of air while the chamber fills with liquid. The chamber is divided into two compartments having different thicknesses by separation wall (3) which has the separation channels (7, 8) on top of it. Two different channels (7), (8) having different size are seen in more detail in FIG. 3. Channel (7) is sized to allow only particles smaller than a certain size to pass and the channel labeled (8) is sized to allow only liquid to pass. It is obvious to one skilled in the art that these channels can be sized appropriately to exclude any desired cell or particle sizes. It is also obvious to one skilled in the art that additional channels of a size different from those shown could be placed to control the ratio of more than one species of cell or particle.

Referring again to FIG. 1, in a preferred embodiment, fluid fills the sample chamber through a channel (9) designed for that purpose and moves into the first compartment (10) of the chamber. Upon proceeding, the liquid encounters a first notch (11) displaced laterally across the flow path. These notches create a momentary barrier to progression of the advancing fluid meniscus until the meniscus has contacted the notch across the whole width of the compartment. Eventually the fluid wets into the notch, allowing the fluid to advance to the next notch (12) where the meniscus is again evened out. The fluid advance continues in this manner until it reaches the separation wall (3) and separation channels (7), (8). The fluid continues to advance through the channels until finally stopping at the far end (13) of the chamber. After the fluid reaches this wall (13) it becomes quiescent, allowing optical examination in the examination areas (4) within the second compartment and (5) within the first compartment.

FIG. 2 shows an isometric view of the sample chamber with the separating channels (7) and (8) disposed laterally across its full width. FIG. 3 shows a detailed isometric view of separating channels (7) and (8).

As can be seen in FIGS. 1 and 2, capillary stops (14), (15), and (16) are located in the moat area in order to hinder travel of any fluid meniscus which may run along the moat, preventing it from becoming rapidly wetted and causing uncontrolled flow. It is obvious to one skilled in the art that alternate embodiments of these features which employ sharp outside corners can be incorporated to hinder meniscus flow in the same manner.

FIG. 4 shows another advantageous embodiment for the separating channels which allow cellular or particulate species to pass through it (17) while allowing a liquid portion devoid of this species to pass through channels disposed in an array alongside the channel (18).

What is claimed is:

1. A method for obtaining a liquid sample forming a monolayer of desired individual cells or particles for optical examination comprising:
   a) providing an apparatus comprising:
      a sample chamber comprising
         two containment walls, at least one of them being transparent for optical examination;
         at least one wall for holding said containment walls at a distance, and enclosing an interior space;
         a separation wall comprising at least a first separation channel that is of sufficient size and dimensions to allow desired cells or particles to pass while excluding larger cells or particles from passing, and a second separation channel, that is of sufficient size and dimensions to exclude desired cells or particles and larger cells or particles from passing while allowing the liquid component of the sample to pass freely, wherein the interior space of said sample chamber is divided into a first compartment and a second compartment by said separation wall, and whereby the distance between said containment walls in the second compartment in the chamber is sized so that individual desired cells or particles present in the sample will form a monolayer when the chamber is filled with the sample;
         a sample entrance into the first compartment; and
         a means for venting the sample chamber during filling;
   b) depositing a liquid sample into the sample entrance of said sample chamber;
   c) allowing the sample to flow from the sample entrance into the first compartment;
   d) allowing the sample to advance to the separation wall and to the separation channels therein;
   e) allowing desired cells or particles in the sample to pass through the first separation channel in the separation wall and allowing the liquid component of the sample to pass through the second separation channel in the separation wall;
   f) allowing the passed sample portion to continue advance until it reaches and stops at the end of the sample chamber; and
   g) obtaining a liquid sample forming a monolayer of desired individual cells or particles.

2. The method according to claim 1 wherein said liquid sample is blood.

3. The method according to claim 1 wherein said first separation channel is 3 to 10 $\mu$m deep by 5 to 50 $\mu$m wide.

4. The method according to claim 1 wherein said second separation channel is 0.5 to 1.5 $\mu$m deep by 50 to 1000 $\mu$m wide.

5. The method according to claim 1 wherein in step (a) of said method, said apparatus provided therein further comprises a plurality of notches displaced laterally across the flow path in the interior space of said sample chamber in order to even out the advancing fluid meniscus.

6. The method according to claim 5 further comprising after step (c), allowing the sample to flow past each notch in the first compartment.

7. The method according to claim 1 wherein in step (a) of said method, said apparatus provided therein further comprises a plurality of notches displaced laterally across the flow path in the first compartment of said sample chamber in order to even out the advancing fluid meniscus.

8. The method according to claim 7 further comprising after step (c), allowing the sample to flow past each notch in the first compartment.

9. The method of claim 1 wherein said second compartment has an internal volume which is smaller than the internal volume of said first compartment.

10. The method of claim 1 wherein said second compartment has a thickness of from 1 to 7 $\mu$m.

11. The method of claim 1 wherein said first compartment has a thickness of from 10 to 50 $\mu$m.

12. The method according to claim 1 wherein in step (a) of said method, said apparatus provided therein further comprises a moat surrounding the sample chamber to allow for adequate venting of air through a multiplicity of venting-channels in said at least one wall for holding said containment walls at a distance, while said sample chamber fills with liquid.

13. The method according to claim 12 wherein in step (a) of said method, said moat in the apparatus provided therein further comprises at least one capillary stop to prevent uncontrolled flow.

14. The method according to claim 12 wherein said liquid sample is blood.

15. The method according to claim 12 wherein said first separation channel is 3 to 10 $\mu$m deep by 5 to 50 $\mu$m wide.

16. The method according to claim 12 wherein said second separation channel is 0.5 to 1.5 $\mu$m deep by 50 to 1000 $\mu$m wide.

17. The method according to claim 12 wherein in step (a) of said method, said apparatus provided therein further comprises a plurality of notches displaced laterally across the flow path in the interior space of said sample chamber in order to even out the advancing fluid meniscus.

18. The method according to claim 17 further comprising after step (c), allowing the sample to flow past each notch in the first compartment.

19. The method according to claim 12 wherein in step (a) of said method, said apparatus provided therein further comprises a plurality of notches displaced laterally across the flow path in the first compartment of said sample chamber in order to even out the advancing fluid meniscus.

20. The method according to claim 19 further comprising after step (c), allowing the sample to flow past each notch in the first compartment.

21. The method of claim 12 wherein said second compartment has an internal volume which is smaller than the internal volume of said first compartment.

22. The method of claim 2 wherein said second compartment has a thickness of from 1 to 7 $\mu$m.

23. The method of claim 12 wherein said first compartment has a thickness of from 10 to 50 $\mu$m.

* * * * *